(12) United States Patent
Dufau et al.

(10) Patent No.: US 6,291,401 B1
(45) Date of Patent: Sep. 18, 2001

(54) ADDITIVE COMPOSITION FOR PLANT PROTECTION

(75) Inventors: Ghislain Dufau, Dax; Jean-Paul Lauilhe, Saint Paul les Dax, both of (FR)

(73) Assignee: Action Pin, Dax (FR)

( * ) Notice: Subject to any disclaimer, the term of this patent is extended or adjusted under 35 U.S.C. 154(b) by 0 days.

(21) Appl. No.: 09/341,876

(22) PCT Filed: Jan. 19, 1998

(86) PCT No.: PCT/FR98/00096

§ 371 Date: Oct. 12, 1999

§ 102(e) Date: Oct. 12, 1999

(87) PCT Pub. No.: WO98/31223

PCT Pub. Date: Jul. 23, 1998

(30) Foreign Application Priority Data

Jan. 20, 1997 (FR) .................................................. 97 00546

(51) Int. Cl.[7] .......................... A01N 25/30; B01F 17/34; B01F 17/38

(52) U.S. Cl. ............................................ 504/363; 516/204
(58) Field of Search ............................... 504/363; 516/204

(56) References Cited

U.S. PATENT DOCUMENTS

| | | | |
|---|---|---|---|
| 4,822,407 | * | 4/1989 | Esposito .................................... 71/94 |
| 5,741,502 | * | 4/1998 | Roberts ..................................... 424/405 |
| 6,010,978 | * | 1/2000 | Lauilhe et al. ......................... 504/116 |
| 6,103,770 | | 8/2000 | Trouve .................................. 514/785 |

FOREIGN PATENT DOCUMENTS

1002598A6   4/1991  (BE) .
2 729 307 * 7/1996  (FR) .

* cited by examiner

Primary Examiner—S. Mark Clardy
(74) Attorney, Agent, or Firm—Wenderoth, Lind & Ponack, L.L.P.

(57) ABSTRACT

The invention concerns the use of a composition containing a mixture of: (i) at least a fatty acid ester or alkoxylated fatty acid; and (ii) at least a terpenic derivative, as additive enhancing the efficacy of an active plant protective substance, in particular herbicide, fungicide, insecticide or regulating growth.

18 Claims, 2 Drawing Sheets

ADDITIVE COMPOSITION FOR PLANT PROTECTION

Figure 1:
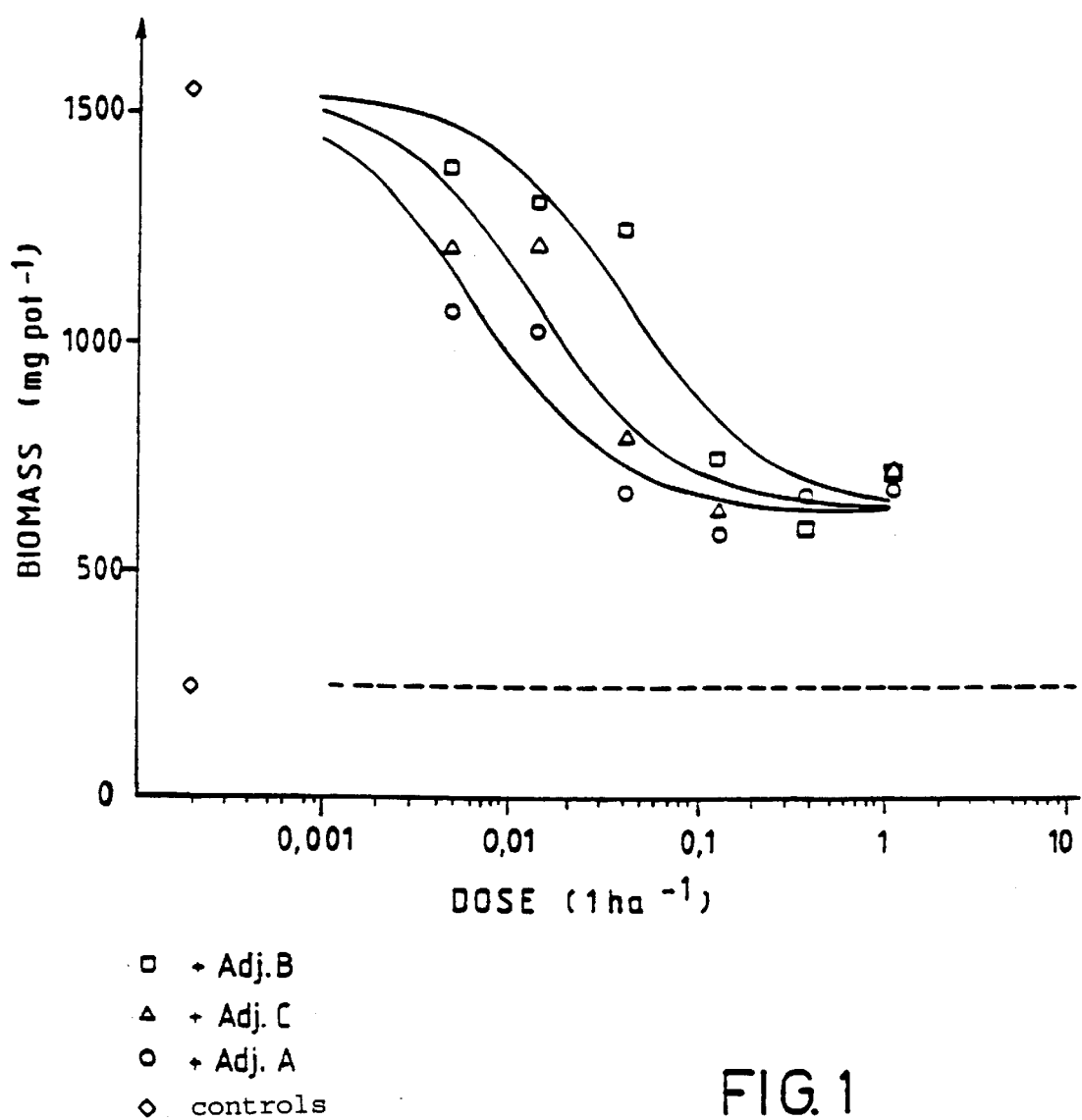

The present invention relates to adjuvants for plant-protection products, in particular fungicides, insecticides, herbicides or growth regulators.

Many plant-protection products are currently available on the market. However, users are constantly seeking more effective treatments.

One route for achieving this consists in using auxiliary agents which, when mixed with plant-protection products, increase the efficacy of the latter products.

These auxiliary agents, which are known globally as "adjuvants" in the text hereinbelow, are typically placed in contact with the active material(s) to be improved in two ways:
 either they form an integral part of the plant-protection preparation sold, referred to as the "plant-protection specialty product" in the text hereinbelow, in which case they will be referred to as the "coformulant";
 or they are added, at the time of use, to the treatment broth usually consisting of a mixture of water and a plant-protection specialty product. This extemporaneous mixture of products can be prepared in a variable order. When used in this way, the adjuvant is referred to as an "adjuvant specialty product" in the text hereinbelow.

The aim of the present invention is to propose novel adjuvants of the coformulant or adjuvant specialty product type which have the property of increasing the efficacy of plant-protection treatments.

A composition comprising copper tallate combined with terpene derivatives is known from FR 91/06753. In this composition, the copper tallate acts as a fungicidal active agent.

A composition comprising a pine oil and a surfactant as adjuvant for a herbicidal composition or broth is also known from FR 93/15653.

It has now been discovered that when a terpene derivative is used in combination with certain fatty acid esters, a pronounced synergistic effect is obtained.

A subject of the invention is thus the use of a composition consisting of a mixture of
 (i) at least one alkoxylated fatty acid or fatty acid ester; and
 (ii) at least one terpene derivative,
  as an adjuvant for improving the efficacy of a plant-protection active substance, in particular a herbicide, fungicide, insecticide or growth regulator.

The fatty acid esters of the invention correspond in particular to the following general formulae:

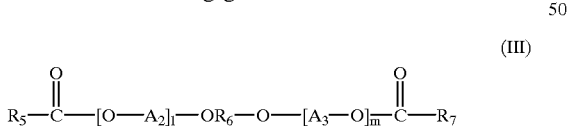

(III)

in which $R_1$, $R_3$, $R_5$, $R_7$, $R_8$, $R_{11}$ and $R_{12}$, which may be identical or different, represent a linear or branched, saturated or unsaturated hydrocarbon-based chain containing from 10 to 30 carbon atoms,
$R_2$, $R_4$, R6, $R_9$ and $R_{10}$, which may be identical or different, represent a linear or branched, saturated or unsaturated hydrocarbon-based chain containing from 1 to 11 carbon atoms, preferably from 1 to 5 carbon atoms,
$A_1$, $A_2$, $A_3$, A4, $A_5$ and $A_6$, which may be identical or different, represent $(CH_2)_2$ or $(CH_2)_3$, and the total number of ethylene oxide or propylene oxide molecules, respectively, in the abovementioned formulae II, III and IV by k, l+m, n+p+q is an integer between 5 and 20, 5 and 30 and 10 and 50, respectively.

Preferably, $R_1$, $R_3$, $R_5$, $R_7$, $R_8$, $R_{11}$ and $R_{12}$, which may be identical or different, are linear or branched hydrocarbon-based groups comprising from 16 to 22 carbon atoms.

Advantageously, these groups are unsaturated and can contain at least one double bond. Mention may be made in particular of oleic acid, linoleic acid and linolenic acid.

Groups which are particularly preferred are those of fatty acids obtained from rapeseed oil, from soybean oil, from sunflower oil, from corn oil, from groundnut oil, from olive oil, from palm oil, from flax oil, from safflower oil, from cottonseed oil, from sesame oil or from tall oil.

Particularly advantageous results are obtained with fatty acid alkyl esters of formula I in which $R_2$ preferably comprises from 1 to 11 carbon atoms.

In this respect, mention may be made of the methyl, ethyl, propyl, isopropyl, butyl, isobutyl, pentyl, hexyl, octyl and branched octyl esters such as the ethylhexyl ester, and those obtained by condensation with decanol.

Other suitable esters are the esters resulting from the condensation of one or more fatty acids as defined above with terpenic alcohols. A terpenic alcohol which may be mentioned in particular is nopol (6,6-dimethylbicyclo[3.1.1]-2-heptene-2-ethanol).

The esters of general formula I according to the invention can be obtained:
 by direct esterification of fatty acids with a monofunctional alcohol;
 by transesterification of plant oils with an alcohol in the presence of the corresponding alkoxide, for example with methanol in the presence of sodium methoxide in the case of the methyl esters.

The esters of general formulae II, III and IV are described in FR 2,729,307.

The compounds of general formulae II, III and IV can be prepared as described in FR 2,729,307.

For the purpose of the present invention, the terpene derivatives are organic molecules containing ten carbon atoms in their structure.

These are thus essentially monoterpenes.

The terpene derivatives can be acyclic, monocyclic or bicyclic.

Mention may be made in particular of the following examples:
 1) terpenic carbides:
  a) acyclic terpenic carbides: myrcene, alloocymene, etc.;
  b) monocyclic terpenic carbides: dipentene, terpinolene, p-cymene, limonene, etc.;
  c) bicyclic terpenic carbides: α-pinene, β-pinene or δ-3-carene, etc.;
 2) the following compounds:
  a- oxidized derivatives: cineols;
  b- terpenic alcohols: borneol, fenchol, menthanol, terpineols, geraniol, etc.;
  c- aldehydes and ketones: camphor, fenchone;
 3) mixtures of the abovementioned products;
 4) pine oils of natural or synthetic origin which are defined as being mixtures of terpenic alcohols and terpenic carbides; and
 5) tea tree oil (or oil of *Melalenca alternifolia*) which is defined as being a mixture of terpenic alcohols (terpinen-4-ol, α-terpineol, etc.), terpenic carbides (α- and δ-terpinene, p-cymene, limonene, etc.) and 1,8-cineol.

Pine oil containing 90% terpenic alcohols is most particularly preferred.

The compositions according to the invention can be used as adjuvant compositions for plant-protection use, in particular for improving the efficacy of a herbicidal, fungicidal, insecticidal or growth-regulating plant-protection active substance.

A composition according to the invention comprises from 80 to 20% by weight, preferably from 60 to 40% by weight, of compound (i) and from 20 to 80% by weight, preferably from 40 to 60% by weight, of compound (ii).

The combination of a composition according to the present invention and a fungicidal, insecticidal, herbicidal or growth-regulating active substance has the effect, surprisingly, of increasing the efficacy of the treatment, which can thus allow a reduced dose of substance to be used.

This latter point and the fact that the base ingredients of a composition according to the present invention are natural product derivatives are factors in favour of better care for the environment.

A composition according to the invention is most particularly effective for improving the properties of a penetrating or systemic active substance, which acts by absorption into the plant.

It can be used, for example, with a herbicidal product based on such a substance which acts by absorption into the plant. Among the families of herbicidal agents, mention may be made of aryloxyphenoxypropionates, cyclohexanediones, diazines, triazines, pyridyl phenyl ethers, triketones, carbamates and benzofuran derivatives, and in particular:

phenoxaprop-p-ethyl, quizalofop-ethyl and its D isomer, diflufenicanil, ioxynil, bromoxynil and mixtures thereof, phenmedipham, ethofumesate, desmedipham and mixtures thereof, clodinafop propargyl and its mixture with a plant-protection agent, cloquintocet mexyl, pyridate, sulcotrione, bentazone, atrazine and mixtures thereof.

It can also be used with a growth regulator, in particular chlormequat chloride used alone or in combination with choline chloride.

A composition according to the invention can typically be used in two ways: in the form of a coformulant or in the form of an adjuvant specialty product, the two terms having been defined previously.

The plant-protection specialty products, as defined above, containing a coformulant consisting of a mixture according to the invention, are also a subject of the invention.

Adjuvant specialty products based on a composition according to the invention are also a subject of the invention. They consist of a composition according to the invention, to which has been added one or more emulsifiers to allow this composition to be dispersed easily in water.

The emulsifiers can be of anionic or nonionic type. Ethoxylated alkylphenols, ethoxylated fatty alcohols, ethoxylated fatty acids, ethoxylated fatty acid esters and ethoxylated triglycerides can be used, for example.

The examples which follow illustrate the invention. The herbicidal broths were prepared using a plant-protection specialty product and an adjuvant specialty product.

The percentages are expressed on a weight basis except where otherwise indicated.

EXAMPLE 1

This test, performed under controlled conditions, compares the effects obtained with three treatment broths containing the same plant-protection specialty product and water, which are respectively mixed with three different adjuvant specialty products.

The three adjuvant specialty products contain the same emulsifier (castor oil ethoxylated with 18/20 EO), in the same proportion (25% by weight):

the adjuvant specialty product B (Adj. B) consists of a mixture of methyl ester of fatty acids from tall oil whose composition is as follows:

| | |
|---|---|
| oleic acid | 53.1% |
| linoleic acid | 36.8% |
| palmitic and stearic acids | 2.4% |
| various fatty acids (palmitoleic, elaidic, pinoleic, arachidic, etc. acids) | 7.7% |
| and of emulsifier. | | the adjuvant specialty product C (Adj. C) consists of a mixture of pine oil containing 90% terpenic alcohols and of emulsifier.

the adjuvant specialty product A (Adj. A) consists of a mixture of 40% adjuvant B and 60% adjuvant C.

The herbicidal plant-protection specialty product used is Celio® from CIBA Plant Protection (clodinafop-propargyl+cloquintocet mexyl).

The sprayings are carried out at a rate of 150 l of broth per hectare. The model weed is oat (Avena sativa). The herbicidal effect is measured by means of the mass of plant solids 10 days after the treatment.

The doses of Celio® applied are 0.005–0.015–0.044–0.13–0.4 and 1.2 l/ha, respectively.

The doses of adjuvants (Adj. B, Adj. C and Adj. A) are 0.5 l/ha.

Figure 2:
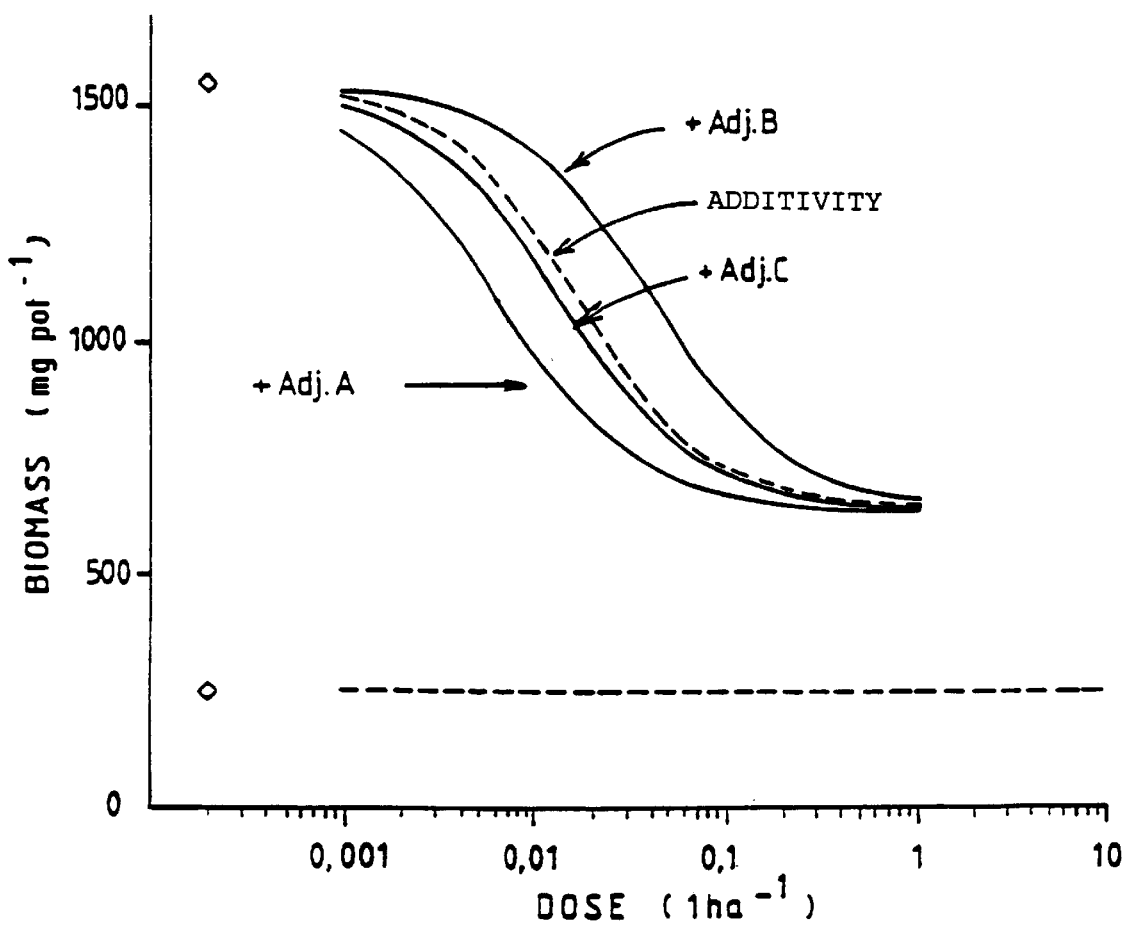

In FIGS. 1 and 2, the curves illustrate the set of responses to variable doses of plant-protection specialty product.

FIG. 1 shows the three curves obtained with the three treatment broths, which differ only in the adjuvant specialty product.

The doses which allow a 50% inhibition ($I_{50}$) to be obtained are, respectively:

broth containing Adj. B=0.044±0.017 l/ha broth containing Adj. C=0.014±0.006 l/ha broth containing Adj. A=0.007±0.003 l/ha the curve of additivity, calculated from the curves corresponding to the treatments containing Adj. B and Adj. C, is added in FIG. 2.

For this calculation model, the model of additivity of doses is used and the ratio of Adj. B and Adj. C in the mixture Adj. A, i.e. 0.4 and 0.6, respectively, is taken into account.

FIG. 2 indicates the relative positions of the additivity curve and of the curve of response to the treatment containing Adj. A.

The response curve is shifted towards low doses relative to the additivity curve, which reflects the synergistic effect.

EXAMPLE 2

Evaluation of the advantage of various adjuvant specialty products in combination with Puma S® from Agrevo (fenoxaprop-p-ethyl) on black-grass (*Alopecurus myosuroides*).

The trials were performed in greenhouses on potted plants, sowing with adventitious plants. The herbicidal treatment was carried out at the 2–4 leaf stage of the adventitious plants. At the end of the trial, the black-grass was cut to weigh the fresh material.

The results are given in Table I below.

TABLE I

| HERBICIDE (dose) | ADJUVANT (dose) | Weight of fresh material |
|---|---|---|
| Puma S (0.6 1/ha) | — | 0.54 g |
| Puma S (0.4 1/ha) | — | 4.71 g |
| Puma S (0.3 1/ha) | — | 8.30 g |
| Puma S (0.3 1/ha) | PO (1 1/ha) | 2.30 g |
| Puma S (0.3 1/ha) | Ester 1 (1 1/ha) | 4.19 g |
| Puma S (0.3 1/ha) | Ester 2 (1 1/ha) | 2.31 g |
| Puma S (0.3 1/ha) | Ester 3 (1 1/ha) | 2.67 g |
| Puma S (0.3 1/ha) | Ester 4 (1 1/ha) | 3.82 g |
| Puma S (0.3 1/ha) | PO (0.5 1/ha) + Ester 1 (0.5 1/ha) | 0.45 g |
| Puma S (0.3 1/ha) | PO (0.S 1/ha) + Ester 2 (0.5 1/ha) | 0.40 g |
| Puma S (0.3 1/ha) | PO (0.5 1/ha) + Ester 3 (0.5 1/ha) | 1.34 g |
| Puma S (0.3 1/ha) | PO (0.5 1/ha) + Ester 4 (0.5 1/ha) | 1.50 g |

PO: Pine oil containing 90% terpenic alcohols + emulsifier (in proportions of 75/25)
Ester 1: Methyl ester of fatty acids from tall oil + emulsifier (in proportions of 75/25)
Ester 2: Butyl ester of fatty acids from tall oil + emulsifier (in proportions of 75/25)
Ester 3: Isobutyl ester of fatty acids from tall oil + emulsifier (in proportions of 75/25)
Ester 4: Ethylhexyl ester of fatty acids from tall oil + emulsifier (in proportions of 75/25)

These various adjuvant specialty products were formulated by adding a nonylphenol ethoxylated with 9/10 EO as emulsifier.

These results show a very pronounced synergistic effect when a mixture of a fatty acid derivative and pine oil is used, according to the invention, in particular when the fatty acid derivative is a methyl or butyl ester.

In Examples 3 to 8 which follow, the adjuvant specialty product A (Adj. A) consists of a mixture of methyl ester of fatty acids from tall oil, pine oil containing 90% terpenic alcohols and castor oil ethoxylated with 18/20 EO (in proportions of 30/45/25).

EXAMPLE 3

Field evaluation of the efficacy of the adjuvant specialty product A (Adj. A) in combination with Puma S® on black-grass in a winter wheat crop.

The results are given in Table II below.

TABLE II

| HERBICIDE (dose) | ADJUVANT (dose) | Visual efficacy on black-grass T + 46 d |
|---|---|---|
| Puma S (1.2 1/ha) | | 53.33% |
| Puma S (1.2 1/ha) | Adj. A (1 1/ha) | 73.33% |
| Puma S (0.9 1/ha) | | 36.67% |
| Puma S (0.9 1/ha) | Adj. A (1 1/ha) | 53.33% |
| Puma S (0.6 1/ha) | | 23.33% |
| Puma S (0.6 1/ha) | Adj. A (1 1/ha) | 53.33% |
| Puma S (0.3 1/ha) | | 13.33% |
| Puma S (0.3 1/ha) | Adj. A (1 1/ha) | 40.00% |

Untreated crop: 60 black-grasses/m$^2$

EXAMPLE 4

Field evaluation of the efficacy of the adjuvant specialty product A (Adj. A) in combination with Celio® on black-grass in a winter wheat crop.

The results are given in Table III below.

TABLE III

| HERBICIDE (dose) | ADJUVANT (dose) | Visual efficacy on black-grass | | |
|---|---|---|---|---|
| | | T + 17 d | T + 34 d | T + 50 d |
| Celio (0.60 1/ha) | | 45.00% | 98.75% | 100% |
| Celio (0.60 1/ha) | Adj. A (1 1/ha) | 65.00% | 99.00% | 100% |
| Celio (0.45 1/ha) | | 43.75% | 98.00% | 100% |
| Celio (0.45 1/ha) | Adj. A (1 1/ha) | 57.50% | 98.00% | 100% |
| Celio (0.30 1/ha) | | 36.25% | 98.00% | 96.00% |
| Celio (0.30 1/ha) | Adj. A (1 1/ha) | 62.50% | 99.00% | 99.75% |
| Celio (0.15 1/ha) | | 26.25% | 62.50% | 53.75% |
| Celio (0.15 1/ha) | Adj. A (1 1/ha) | 58.75% | 99.00% | 98.25% |

Untreated crop: 303 black-grasses/m$^2$

EXAMPLE 5

Field evaluation of the efficacy of the adjuvant specialty product A (Adj. A) in combination with Lentagran® from Sandoz Agro (pyridate), Mikado® from Sopra (sulcotrione) or Laddok® from BASF France (bentazone+atrazine) against dicotyledons and dicotyledons+graminaceas in a corn crop.

The results are given in Table IV below.

TABLE IV

| | | Visual efficacy | | | |
|---|---|---|---|---|---|
| | | On dicotyledons | | On dicotyledons + graminaceas | |
| HERBICIDE (dose) | ADJUVANT (dose) | T + 13 d | T + 24 d | T + 13 d | T + 24 d |
| Lentagran A (1.5 1/ha) | | 90.0% | 90.0% | 50.0% | 50.0% |
| Lentagran A (0.75 1/ha) | | 88.3% | 63.3% | 50.0% | 33.3% |
| Lentagran A (0.75 1/ha) | Adj. A (1 1/ha) | 90.0% | 90.0% | 50.0% | 50.0% |
| Mikado (1 1/ha) | | 93.3% | 96.0% | 88.3% | 90.0% |
| Mikado (0.5 1/ha) | | 25.0% | 56.7% | 33.3% | 66.7% |
| Mikado (0.5 1/ha) | Adj. A (1 1/ha) | 97.7% | 96.3% | 86.7% | 86.7% |
| Laddok (3 1/ha) | | 98.0% | 97.7% | 50.0% | 50.0% |
| Laddok (1.5 1/ha) | | 91.0% | 84.3% | 43.3% | 43.3% |
| Laddok (1.5 1/ha) | Adj. A (1 1/ha) | 95.7% | 97.0% | 46.7% | 50.0% |

Untreated crop:
107 large crabgrass (*Digitaria Sanguinalis*) plants/m$^2$
118 common lambsquarters (*Chenopodium album*) plants/m$^2$
27 pale smartweed (*Polygonum tomentosum*) plants/m$^2$
3 redroot pigweed (*Amaranthus retroflexus*) plants/m$^2$

EXAMPLE 6

Field comparison of the efficacy of the adjuvant specialty product A (Adj. A) in combination with Betanal Progress® from Agrevo (phenmedipham+desmedipham+ethofumesate) on field violet (Viola arvensis) and annual mercury (*Mercurialis annua*), in. beetroot crops.

The results are given in Table V below.

TABLE V

| HERBICIDE (dose) | ADJUVANT (dose) | Visual efficacy | |
|---|---|---|---|
| | | T + 8 d | T + 15 d |
| Betanal Progress (5 1/ha) | | 72.50% | 47.50% |
| Betanal Progress (5 1/ha) | Adj. A (1 1/ha) | 73.75% | 75.00% |
| Betanal Progress (3.75 1/ha) | | 66.25% | 63.75% |
| Betanal Progress (3.75 1/ha) | Adj. A (1 1/ha) | 71.25% | 63.75% |
| Betanal Progress (2.5 1/ha) | | 25.00% | 26.25% |
| Betanal Progress (2.5 1/ha) | Adj. A (1 1/ha) | 63.75% | 52.50% |
| Betanal Progress (1.25 1/ha) | | 12.50% | 15.00% |
| Betanal Progress (1.25 1/ha) | Adj. A (1 1/ha) | 8.75% | 17.50% |

Untreated crop:
32 field violet plants/m$^2$
15 annual mercury plants/m$^2$

EXAMPLE 7

Field comparison of the efficacy of the adjuvant specialty product A (Adj. A) in combination with Targa D+® from Rhône-Poulenc Agro (quizalofop ethyl, D isomer) on proteaginous peas.

The results are given in Tables VI and VII below.

TABLE VI

| HERBICIDE (dose) | ADJUVANT (dose) | Visual efficacy on blue grasses | | |
|---|---|---|---|---|
| | | T + 10 d | T + 30 d | T + 51 d |
| Targa D+ (1.25 1/ha) | | 70.0% | 83.3% | 76.7% |
| Targa D+ (1.25 1/ha) | Adj. A (1 1/ha) | 80.0% | 85.0% | 80.0% |
| Targa D+ (1.25 1/ha) | Adj. A (2 1/ha) | 80.0% | 86.7% | 83.3% |

TABLE VII

| HERBICIDE (dose) | ADJUVANT (dose) | Visual efficacy on raygrass at T + 9 d |
|---|---|---|
| Targa D+ (1.25 1/ha) | | 66.7% |
| Targa D+ (0.6 1/ha) | | 43.3% |
| Targa D+ (0.6 1/ha) | Adj. A (0.5 1/ha) | 53.3% |
| Targa D+ (0.6 1/ha) | Adj. A (0.75 1/ha) | 56.7% |
| Targa D+ (0.6 1/ha) | Adj. A (1 1/ha) | 68.3% |

EXAMPLE 8

Field comparison of the efficacy of the adjuvant specialty product A (Adj. A) in combination with Cycocel C5® from BASF (chlormequat chloride+choline chloride) on straw cereals, Sideral variety very sensitive to eyespot.

The results are given in Table VIII below:

TABLE VIII

| SHORTENER (dose) | ADJUVANT (dose) | Observations at T + 46 d | | |
|---|---|---|---|---|
| | | Number of ears/m$^2$ | Height of plant in cm | % of the control |
| Untreated crop | | 371 | 83.4 | 100% |
| Cycocel C5 (2 1/ha) | | 361 | 80.9 | −3% |
| Cycocel C5 (2 1/ha) | Adj. A (0.5 1/ha) | 376 | 76.6 | −9% |
| Cycocel C5 (2 1/ha) | Adj. A (1 1/ha) | 395 | 74.6 | −10.5% |

What is claimed is:

1. A composition comprising:

(i) at least one alkoxylated fatty acid ester of the formula:

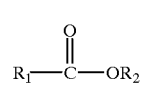

(I)

in which R$_1$ represents a linear or branched, saturated or unsaturated hydrocarbon chain containing from 10 to 30 carbon atoms, and R$_2$ represents a linear or branched, saturated or unsaturated hydrocarbon chain containing from 1 to 11 carbon atoms; and (ii) at least one terpene.

2. The composition according to claim 1, in which R$_2$ represents methyl, ethyl, propyl, isopropyl, butyl, isobutyl, pentyl, hexyl, octyl, ethylhexyl, decyl or terpenyl.

3. The composition according to claim 1, wherein R$_1$ represents a linear or branched, saturated or unsaturated, C$_{16}$–C$_{22}$ hydrocarbon chain.

4. The composition according to claim 1, wherein R$_1$ represents an unsaturated C$_{16}$–C$_{22}$ hydrocarbon chain.

5. The composition according to claim 1, wherein R$_1$ represents a chain of a fatty acid obtained from rapeseed oil, soybean oil, sunflower oil, corn oil, groundnut oil, olive oil, palm oil, flax oil, safflower oil, cottonseed oil, sesame oil or tall oil.

6. The composition according to claim 1, wherein said compound of general formula I is selected from the group consisting of methyl, butyl, isobutyl and ethylhexyl esters.

7. A composition according to claim 1, wherein said compound of general formula I is a methyl ester of a fatty acid mixture of tall oil.

8. The composition according to claim 1, wherein said terpene derivative is a monoterpene or a mixture of monoterpenes.

9. The composition according to claim 1, wherein said terpene derivative is selected from the group consisting of terpenic carbides, oxidized derivatives of terpenic carbides, terpenic alcohols, terpenic aldehydes and ketones, and mixtures thereof.

10. The composition according to claim 1, wherein said terpene derivative is a mixture of terpenic carbides and terpenic alcohols.

11. The composition according to claim 1, wherein said terpene derivative is a pine oil.

12. The composition according to claim 1, where said terpene derivative is a pine oil containing 90% terpenic alcohols.

13. The composition according to claim 1, wherein $R_2$ contains 1 to 5 carbon atoms.

14. The composition according to claim 1 containing 80 to 20% of compound (i) and 20 to 80% of compound (ii).

15. The composition according to claim 1 comprising 60 to 40% of compound (i) and 40 to 60% of compound (ii).

16. The composition according to claim 1 which consists of:
   (i) a methyl ester of a fatty acid mixture of tall oil; and
   (ii) pine oil containing 90% terpenic alcohols.

17. A herbicidal composition comprising a herbicide and the composition of any of claims 1 to 16.

18. A herbicidal method which comprises applying the composition of claim 17 to an area to be treated in an effective amount to achieve herbicidal activity in said area.

* * * * *